United States Patent
Park et al.

(10) Patent No.: US 7,794,858 B2
(45) Date of Patent: Sep. 14, 2010

(54) PHENYLPHENOXAZINE OR PHENYLPHENOTHIAZINE- BASED COMPOUND AND ORGANIC ELECTROLUMINESCENT DEVICE USING THE SAME

(75) Inventors: Sang-hoon Park, Seongnam-si (KR);
O-hyun Kwon, Yongin-si (KR);
Woon-jung Paek, Yongin-si (KR)

(73) Assignees: Samsung Electronics Co., Ltd. (KR);
Samsung Mobile Display Co., Ltd. (KR)

( * ) Notice: Subject to any disclaimer, the term of this patent is extended or adjusted under 35 U.S.C. 154(b) by 372 days.

(21) Appl. No.: 12/043,522

(22) Filed: Mar. 6, 2008

(65) Prior Publication Data
US 2009/0026928 A1    Jan. 29, 2009

(30) Foreign Application Priority Data
Jul. 24, 2007    (KR) .................... 10-2007-0074125

(51) Int. Cl.
*H01J 63/04*    (2006.01)
*C07D 413/12*    (2006.01)

(52) U.S. Cl. .................... 428/690; 544/102; 544/37; 313/504

(58) Field of Classification Search .............. None
See application file for complete search history.

(56) References Cited

U.S. PATENT DOCUMENTS

| 4,356,429 | A | 10/1982 | Tang |
| 4,885,211 | A | 12/1989 | Tang et al. |
| 5,151,629 | A | 9/1992 | VanSlyke |
| 6,541,129 | B1 | 4/2003 | Kawamura et al. |
| 2006/0166038 | A1 * | 7/2006 | Park et al. .................... 428/690 |

OTHER PUBLICATIONS

Kuwabara, Yoshiyuki, et al., Thermally Stable Multilayered Organic Electroluminescent Devices Using Novel Starburst Molecules . . . , Advanced Materials, 1994, 6, No. 9, pp. 677-679.

* cited by examiner

*Primary Examiner*—D. Lawrence Tarazano
*Assistant Examiner*—Gregory Clark
(74) *Attorney, Agent, or Firm*—Cantor Colburn LLP (57) ABSTRACT

Provided are a phenylphenoxazine- or phenylphenothiazine-based compound and an organic electroluminescent device using the same. The phenylphenoxazine- or phenylphenothiazine-based compound is easily prepared, easily dissolved, and has excellent hole injection properties and excellent thermal stability. Accordingly, the compound is suitable for an organic layer of the organic electroluminescent device, specifically, a hole injection layer or a hole transport layer. In addition, the compound is suitable for an organic pigment or an electronic material, such as a nonlinear optical material.

5 Claims, 2 Drawing Sheets

PHENYLPHENOXAZINE OR PHENYLPHENOTHIAZINE- BASED COMPOUND AND ORGANIC ELECTROLUMINESCENT DEVICE USING THE SAME

This application claims priority to Korean Patent Application No. 10-2007-0074125, filed on Jul. 24, 2007, in the Korean Intellectual Property Office, the disclosure of which is incorporated herein in its entirety by reference.

BACKGROUND OF THE INVENTION

1. Field of the Invention

The present disclosure relates to a phenylphenoxazine or phenylphenothiazine-based compound and an organic electroluminescent device comprising the same.

2. Description of the Related Art

Organic electroluminescent devices are self-emissive display devices that emit light generated by the recombination of electron and holes in a fluorescent or phosphorescent organic compound thin layer (hereinafter, referred to as an organic layer) when a current is provided to the organic layer. Organic electroluminescent devices have only a few components and thus can be manufactured to be light in weight, using simple manufacturing processes. In addition, organic electroluminescent devices produce high quality images and have wide viewing angles. Furthermore, organic electroluminescent devices can be used in mobile devices to provide images of high quality, and high color purity, at low levels of electric power and at low operation voltages. Due to these and other advantages, organic electroluminescent devices have electrical properties suitable for use in portable electronic devices.

Eastman Kodak Co. in U.S. Pat. No. 4,885,211 has disclosed an organic electroluminescent device having a multilayer structure comprising an aluminum quinolinol complex layer and a triphenylamine derivative layer. U.S. Pat. No. 5,151,629 discloses that the use of a low molecular weight molecule for an organic emission layer enables a wider emission range from an ultraviolet light region to an infrared light region.

Light-emitting devices are self-emissive devices. Light-emitting devices have wide viewing angles, excellent contrast properties, and quick response speeds. Light-emitting devices can be categorized into inorganic light emitting devices comprising an emission layer formed of an inorganic compound, and organic light emitting devices (OLED) comprising an emission layer formed of an organic material. OLEDs have better brightness, smaller operation voltages, and quicker response speeds than inorganic light emitting devices. In addition, OLEDs can provide various colors. Due to these advantages of OLEDs, extensive research into the development and use of OLEDs is currently being performed.

In general, OLEDs have a basic stack structure comprising an anode an organic emission layer, and a cathode. In addition, OLEDs can have other various structures. Examples of such stack structures include an anode/a hole injection layer/a hole transport layer/an emission layer/an electron transport layer/an electron injection layer/a cathode, or an anode/a hole injection layer/a hole transport layer/an emission layer/a hole blocking layer/an electron transport layer/an electron injection layer/a cathode.

In cases where an organic electroluminescent device is used in a display device, low levels of power consumption can be obtained when the same emission efficiency is obtained under a low operating voltage, or when a high emission efficiency is obtained under the same operating voltage.

U.S. Pat. No. 4,356,429 discloses a phthalocyanine compound, such as copper phthalocyanine, for use as a hole-injecting material. Advanced Materials, vol. 6, p. 677 (1994) also discloses star-burst amine derivatives, such as 4,4',4"-tri (N-carbazolyl)triphenylamine (TCTA), 4,4',4"-tris[N,N-(m-tolyl)phenylamino]triphenylamine (m-MTDATA), or 1,3,5-tris[4-(3-methylphenylphenylamino)phenyl]benzene (m-MTDAPB), for use as hole injecting materials. The use of these compounds as hole-injecting materials decreases the operating voltage of the organic electroluminescent device. However, in each of these cases, sufficient lifetime, efficiency, and electrical power consumption cannot be obtained.

A material disclosed in U.S. Pat. No. 6,541,129 shows excellent organic electroluminescent properties as compared to prior art materials, but does not show sufficient thermal stability due to its low glass transition temperature.

SUMMARY OF THE INVENTION

The present disclosure provides a compound that can be treated using both dry and wet processes. The compound decreases the operation voltage of an organic electroluminescent device, and also has a high glass transition temperature, excellent thermal stability thereby preventing crystallization of the compound, excellent electrical stability, and high charge flow properties.

The present disclosure also provides an organic electroluminescent device comprising an organic layer comprising the compound, wherein the organic electroluminescent device has high efficiency, low voltage, high brightness, and a long lifetime.

According to one embodiment, there is provided a phenylphenoxazine- or phenylphenothiazine-based compound represented by Formula 1:

[Formula 1]

wherein in Formula 1, $R_1$ through $R_9$ are identical to or different from each other, and are each independently hydrogen, a halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{30}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ aralkyl group, or a substituted or unsubstituted $C_2$-$C_{30}$ heteroaryl group; X is O or S; and $Ar_1$ and $Ar_2$ are identical to or different from each other, and are each independently a substituted or unsubstituted $C_6$-$C_{30}$ aryl group, or a substituted or unsubstituted $C_2$-$C_{30}$ heteroaryl group.

According to another embodiment, there is provided an organic electroluminescent device comprising: a first electrode; a second electrode; and at least one organic layer interposed between the first electrode and the second electrode, wherein the organic layer comprises the compound represented by Formula 1.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

It will be understood that when an element or layer is referred to as being "on," "interposed," "disposed," or "between" another element or layer, it can be directly on, interposed, disposed, or between the other element or layer or intervening elements or layers can be present.

In one embodiment, a phenylphenoxazine- or phenylphenothiazine-based compound represented by Formula 1 is provided:

[Formula 1]

wherein in Formula 1, $R_1$ through $R_9$ are identical to or different from each other, and are each independently hydrogen, a halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{30}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ aralkyl group, or a substituted or unsubstituted $C_2$-$C_{30}$ heteroaryl group; X is O or S; and $Ar_1$ and $Ar_2$ are identical to or different from each other, and are each independently a substituted or unsubstituted $C_6$-$C_{30}$ aryl group, or a substituted or unsubstituted $C_2$-$C_{30}$ heteroaryl group.

The aryl group is a monovalent group having an aromatic cyclic system, and can comprise a cyclic system having two or more rings. The two or more rings can be bound to or fused to each other. The heteroaryl group refers to an aryl group in which one or more carbon atoms are substituted with one or more atoms selected from N, O, S or P.

The cycloalkyl group refers to an alkyl group having a cyclic system, and the heterocycloalkyl group refers to a cycloalkyl group in which one or more carbon atoms are selected from N, O, S or P.

In Formula 1, when the alkyl group, the alkoxy group, the aryl group, the aralkyl group, the heteroaryl group, the cycloalkyl group and the heterocycloalkyl group are substituted, their substituent can be one of F; Cl; Br; CN; $NO_2$; OH; a $C_1$-$C_{20}$ alkyl group that is unsubstituted or substituted with F, Cl, Br, CN, $NO_2$ or OH; a $C_1$-$C_{20}$ alkoxy group that is unsubstituted or substituted with F, Cl, Br, CN, $NO_2$ or OH; a $C_6$-$C_{30}$ aryl group that is unsubstituted or substituted with a $C_1$-$C_{20}$ alkyl group, a $C_1$-$C_{20}$ alkoxy group, F, Cl, Br, CN, $NO_2$ or OH; a $C_2$-$C_{30}$ heteroaryl group that is unsubstituted or substituted with a $C_1$-$C_{20}$ alkyl group, a $C_1$-$C_{20}$ alkoxy group, F, Cl, Br, CN, $NO_2$ or OH; a $C_5$-$C_{20}$ cycloalkyl group that is unsubstituted or substituted with a $C_1$-$C_{20}$ alkyl group, a $C_1$-$C_{20}$ alkoxy group, F, Cl, Br, CN, $NO_2$ or OH; a $C_5$-$C_{30}$ heterocycloalkyl group that is unsubstituted or substituted with a $C_1$-$C_{20}$ alkyl group, a $C_1$-$2_0$ alkoxy group, F, Cl, Br, CN, $NO_2$ or OH; a group represented by $N(G_6)(G_7)$; or a combination comprising at least one of the foregoing substituents. In the substituent $N(G_6)(G_7)$, $G_6$ and $G_7$ can be identical to or different from each other, and are each independently hydrogen; a $C_1$-$C_{10}$ alkyl group; or a $C_6$-$C_{30}$ aryl group substituted with a $C_1$-$C_{10}$ alkyl group.

Exemplary embodiments of the compound of Formula 1 include compounds represented by Formulae 2 through 13, but are not limited thereto:

[Formula 2]

[Formula 3]

[Formula 4]

[Formula 8]

[Formula 5]

[Formula 9]

[Formula 6]

[Formula 10]

[Formula 7]

[Formula 11]

-continued

[Formula 12]

[Formula 13]

In another embodiment, the phenylphenoxazine- or phenylphenothiazine-based compounds have excellent hole transporting capabilities due to their delocalized electron distribution. In addition, the phenylphenoxazine- or phenylphenothiazine-based compounds have high glass transition temperatures. High glass transition temperatures result from the binding of a nitrogen atom of a phenylbenzidine to a phenylphenoxazine or phenylphenothiazine substituent, thereby resulting in excellent thermal stability.

The compound represented by Formula 1 can be prepared by reacting phenylphenoxazinebromide, or phenylphenothiazinebromide as represented by Formula 14, with N,N-diarylbenzidine as represented by Formula 15.

-continued

Formula 1 wherein in Formulas 14 and 15, $R_1$ through $R_9$ are identical to or different from each other, and are each independently hydrogen, a halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{30}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ aralkyl group, or a substituted or unsubstituted $C_2$-$C_{30}$ heteroaryl group; X is O or S; and $Ar_1$ and $Ar_2$ are identical to or different from each other, and are each independently a substituted or unsubstituted $C_6$-$C_{30}$ aryl group, or a substituted or unsubstituted $C_2$-$C_{30}$ heteroaryl group.

The phenylphenoxazinebromide or phenylphenothiazinebromide can be formed from either a phenoxazine or a phenothiazine, by substituting a hydrogen atom at the nitrogen atom with a phenyl group, and then brominating the substituted product.

This synthesis process will be described in detail with reference to the Reaction Schemes used in the Synthesis Examples.

In one embodiment, an organic electroluminescent device is provided comprising a first electrode; a second electrode;

and an organic layer interposed between the first electrode and the second electrode, in which the organic layer comprises one or more of the compounds represented by Formula 1.

The compound represented by Formula 1 may be suitable for forming an organic layer of an organic electroluminescent device, specifically, a hole injection layer or a hole transport layer.

In other comparative organic electroluminescent devices, the stability of an organic layer is reduced when the organic layer is prepared using a solution method. In contrast, the organic electroluminescent device described herein comprises a compound suitable for forming an organic layer having excellent solubility, excellent thermal stability, and excellent overall stability, when prepared using a solution method. Thus, the organic electroluminescent device possesses excellent emission properties, such as excellent operation voltage and high color purity.

In another embodiment, the organic electroluminescent device can comprise various types of structures. Specifically, one or more layers selected from a hole injection layer, a hole transport layer, a hole blocking layer, an electron blocking layer, an electron transport layer, an electron injection layer, or a combination comprising at least one of the foregoing layers, can be further formed between the first electrode and the second electrode.

Figure 1:
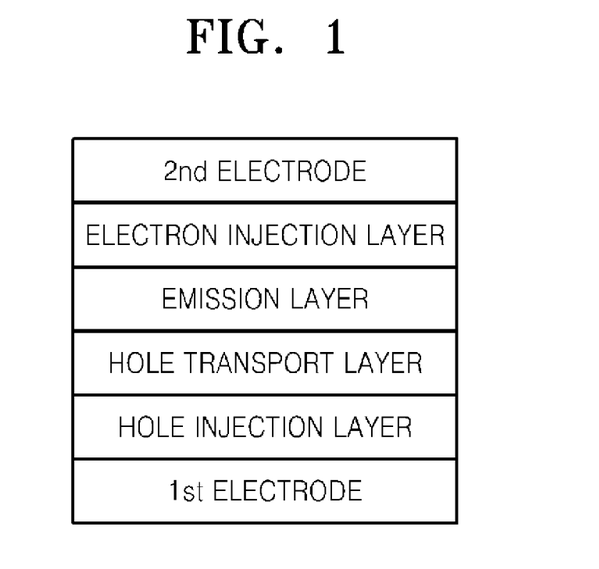
FIG. 1 is a schematic view of an exemplary stack structure of an organic electroluminescent device.

More specifically, the structure of the organic electroluminescent device can be described with reference to FIG. 1. The organic electroluminescent device illustrated in FIG. 1 has the structure comprising a first electrode/a hole injection layer/a hole transport layer/an emission layer/an electron injection layer/a second electrode. In one embodiment, the hole injection layer, the hole transport layer, or a combination comprising both layers, can be formed of the compound represented by Formula 1.

In yet another embodiment, the emission layer of the organic electroluminescent device comprises a red phosphorescent or fluorescent dopant, a green phosphorescent or fluorescent dopant, a blue phosphorescent or fluorescent dopant, or a white phosphorescent or fluorescent dopant. Examples of the phosphorescent dopant include an organometallic compound comprising elements selected from Ir, Pt, Os, Ti, Zr, Hf, Eu, Tb Tm, or a combination comprising at least one of the foregoing elements.

In one embodiment, a method of manufacturing an organic electroluminescent device is provided, and is herein described in detail with reference to FIG. 1.

First, a first electrode forming material having a high work function is formed on a substrate using a deposition method or a sputtering method to form a first electrode. The first electrode can act as an anode. Herein, the substrate can be any known substrate that is used in the manufacture of organic electroluminescent devices. For example, the substrate can be formed of a transparent material having high mechanical stability, high thermal stability, a smooth surface, waterproof, and can be easily handled. Examples of transparent substrates include transparent inorganic substrates, such as quartz and glass; and transparent plastic substrates, such as polyethylene terephthalate ("PET"), polyethylene naphthalate ("PEN"), polycarbonate, polystyrene, polypropylene, polymethylmethacrylate, polyethersulfone ("PES"), and the like; and a combination comprising at least one of the foregoing transparent substrates. Materials that are suitable for the first electrode can be a material that is both transparent and highly conductive. Examples of transparent, highly conductive materials include indium tin oxide (ITO), indium zinc oxide (IZO), tin oxide ($SnO_2$), or zinc oxide (ZnO).

Then, a hole injection layer (HIL) can be formed on the first electrode using methods known to those of skill in the art. Examples of methods that can be used in forming the hole injection layer include a vacuum deposition method, a spin coating method, a casting method, or an LB method.

When the HIL is formed using a vacuum deposition method, the conditions for deposition vary according to the type of compound to be used to form the HIL, and according to the structure and thermal properties of the HIL to be formed. Specifically, the conditions for the vacuum deposition comprise a deposition temperature of about 100 to about 500° C., a degree of vacuum of about $10^{-8}$ to about $10^{-3}$ Torr, and a vacuum pumping speed of about 0.01 to about 100 liters/sec. The thickness of the formed HIL is about 10 Angstroms to about 5 micrometers (μm).

When the HIL is formed using a spin coating method, the coating conditions vary according to the type of compound used to form the HIL, and according to the structure and thermal properties of the HIL to be formed. Specifically, the conditions for the spin coating comprise a coating speed of about 2000 rotations per minutes (rpm) to about 5000 rpm. An effective temperature for a heat-treating process to remove solvent following the coating process, about 80° C. to about 200° C.

The HIL forming material can be the compound represented by Formula 1 described above. The thickness of the HIL may be about 100 Angstroms to about 10,000 Angstroms, specifically from about 100 Angstroms to about 1000 Angstroms. When the thickness of the HIL is less than about 100 Angstroms, the hole injection properties of the layer may be degraded. On the other hand, when the thickness of the HIL is greater than about 10000 Angstroms, the operating voltage of the organic electroluminescent device may be increased.

A hole transport layer (HTL) can then be formed on the HIL using a vacuum deposition method, a spin coating method, a casting method, or a LB method.

When the HTL is formed using a vacuum deposition method or a spin coating method, the deposition conditions and the coating conditions vary according to the type of compound used. Specifically, the deposition conditions and the coating conditions are similar to the deposition and coating conditions that are used to form the HIL.

The HTL forming material can be the compound represented by Formula 1 described above. The thickness of the HTL may be about 50 Angstroms to about 1000 Angstroms, specifically about 100 Angstroms to about 600 Angstroms. When the thickness of the HTL is less than about 50 Angstroms, the hole transport properties of the layer may be degraded. On the other hand, when the thickness of the HTL is higher than about 1000 Angstroms, the operating voltage of the organic electroluminescent device may be increased.

An emission layer (EML) can then be formed on the HTL using a vacuum deposition method, a spin coating method, a casting method, or a Langmuir-Blodgett (LB) method. When the EML is formed using a vacuum deposition method or a spin coating method, the deposition conditions and the coating conditions vary according to the type of compound used. Specifically, the deposition conditions and the coating conditions are similar to the deposition and coating conditions which are used to form the HIL.

The EML forming material can be the compound represented by Formula 1 described above. In some cases, however, the compound can be used together with any fluorescent host material that is known in the art, or with any dopant material that is known in the art. The concentration of the doping material is not limited. For example, the amount of a dopant may be about 0.01 to about 15 parts by weight based on 100 parts by weight of the fluorescent host material.

The thickness of the EML may be about 100 Angstroms to about 1000 Angstroms, specifically about 200 Angstroms to about 600 Angstroms. When the thickness of the EML is less than about 100 Angstroms, the emission properties of the layer may be degraded. On the other hand, when the thickness of the EML is greater than about 1000 Angstroms, the operating voltage of the organic electroluminescent device may be increased.

An electron injection layer can be formed using any material that is known in the art. Examples of material that can be used to form the electron injection layer include LiF, NaCl, CsF, $Li_2O$, BaO, or a combination comprising at least one of the foregoing electron injection layer materials. The deposition conditions used for forming the electron injection layer vary according to the type of compound used. For example, the deposition conditions used for forming the electron injection layer are similar to the deposition conditions used for forming the HIL.

The thickness of the electron injection layer may be about 1 Angstroms to about 100 Angstroms, specifically about 5 Angstroms to about 50 Angstroms. When the thickness of the electron injection layer is less than about 1 Angstroms, the electron injection properties of the layer may be degraded. On the other when the thickness of the electron injection layer is greater than about 100 Angstroms, the operating voltage of the organic electroluminescent device may be increased.

Finally, a second electrode can be formed on the electron injection layer using a vacuum deposition method or a sputtering method. The second electrode can act as a cathode. The material used to form the second electrode can be a metal, which has a low work function, an alloy, which has a low work function, an electrically conductive compound which has a low work function, or a mixture thereof. Examples of the second electrode forming material include be lithium (Li), magnesium (Mg), aluminium (Al), aluminium-lithium (Al—Li), calcium (Ca), magnesium-indium (Mg—In), magnesium-silver (Mg—Ag), or a combination comprising at least one of the foregoing second electrode materials. In one embodiment, the second electrode in a top emission type light-emitting device, is a transmissive cathode formed of, for example, ITO or IZO.

The present invention will be described in further detail with reference to the following examples. These examples are for illustrative purposes only and are not intended to limit the scope of the present invention.

EXAMPLE

Intermediate 1

Intermediate 2

Intermediate 2

(4)

Intermediate 3

Intermediate 4

Intermediate 4

(9)

Synthesis Example 1

1) Synthesis of Intermediate 1

11.2 grams (g) (65 millimole (mmol)) of 1-bromotoluene, 9.8 g (54 mmol) of phenoxazine, 5.76 g of sodium tert-butoxide, 0.732 g Tris(dibenzylidine acetone) dipalladium(0) ($Pd_2(dba)_3$), and 0.2 g of tri(tert-butyl)phosphine were dissolved in 250 milliliters (ml) of toluene, and then the mixture was reacted at 80° C. for 12 hours.

After the reaction was completed, the reaction mixture was cooled to room temperature and 200 ml of distilled water was added thereto. Then, an extracting process was performed using toluene and water in a volumetric ratio of 1:1. The collected organic layer was dried over $MgSO_4$ and then concentrated. Silica gel column chromatography was performed on the concentrated product using an eluent consisting of toluene and hexane in a volumetric ratio of 1:2. The obtained eluate was concentrated and dried to obtain 11 g (Yield: 73.8%) of Intermediate 1.

$^1$H-NMR (300 MHz, $CDCl_3$): δ 2.75 (m, 3H), 5.72 (d, 2H), 6.65 (d, 2H), 6.65 (d, 2H), 6.71 (d, 2H), 7.08 (d, 2H), 7.25 (d, 2H)

2) Synthesis of Intermediate 2

4.5 g (16.47 mmol) of Intermediate 1 was dissolved in 150 ml of $CHCl_3$. Subsequently, 1 equivalent of bromine, with respect to Intermediate 1, was slowly added thereto at a temperature of 0° C. Then, thin layer chromatography (TLC) was used to determine whether the starting material had been removed. When the starting material was finally removed, the addition of bromine was stopped. The reaction mixture was stirred for an additional 10 minutes and then the reaction was stopped.

A small amount of acetone was added to the reaction mixture to quench the bromine, and an extraction process was then performed using water and $CHCl_3$ in a volumetric ratio of 2:1. The collected organic layer was dried over $MgSO_4$ and concentrated. The concentrated product was precipitated using MeOH. As a result, 3.85 g (Yield: 66%) of Intermediate 2 was obtained.

$^1$H-NMR (300 MHz, $CDCl_3$): δ 2.75 (m, 3H), 5.72 (d, 2H), 6.65 (d, 2H), 6.65 (d, 2H), 6.71 (d, 1H), 7.08 (d, 2H), 7.25 (d, 2H)

3) Synthesis of Compound 4

3.0 g (8.54 mmol) of Intermediate 2, 1.15 g (3.42 mmol) of N,N-diphenylbenzidine, 1.0 g of sodium tert-butoxide, 0.115 g of $Pd_2(dba)_3$, and 0.034 g of tri(tert-butyl)phosphine, were dissolved in 250 ml of toluene, and the mixture was reacted at 80° C. for 12 hours.

After the reaction was complete, the reaction mixture was cooled to room temperature and 200 ml of distilled water was added. Then, an extraction process was performed using toluene and water in a volumetric ratio of 1:1. The collected organic layer was dried over $MgSO_4$ and then concentrated. Silica gel column chromatography was performed on the concentrated product using an eluent of toluene and hexane in a volumetric ratio of 1:2. The obtained eluate was concentrated and dried to obtain 2.8 g (Yield: 93%) of the compound represented by Formula 4.

$^1$H-NMR (300 MHz, $CDCl_3$): δ 2.75 (m, 3H), 5.72 (d, 2H), 6.65 (d, 2H), 6.65 (d, 2H), 6.71 (d, 1H), 7.08 (d, 2H), 7.25 (d, 2H)

Synthesis Example 2

1) Synthesis of Intermediate 3

11.2 g (65 mmol) of 1-bromotoluene, 10.7 g (54 mmol) of phenothiazine, 5.76 g of sodium tert-butoxide, 0.732 g of $Pd_2(dba)_3$ [(Tris(dibenzylidine acetone) dipalladium(0))], and 0.2 g of tri(tert-butyl)phosphine were dissolved in 250 ml of toluene, and then the mixture was reacted at 80° C. for 12 hours.

After the reaction was complete, the reaction mixture was cooled to room temperature and 200 ml of distilled water was added thereto. Then, an extraction process was performed using toluene and water in a volumetric ratio of 1:1. The collected organic layer was dried over $MgSO_4$ and then concentrated. Silica gel column chromatography was performed on the concentrated product using an eluent of toluene and hexane in a volumetric ratio of 1:2. The obtained eluate was concentrated and dried to obtain 12 g (Yield: 77%) of Intermediate 3.

2) Synthesis of Intermediate 4

4.5 g (15.5 mmol) of Intermediate 3 was dissolved in 150 ml of $CHCl_3$, and 1 equivalent of bromine with respect to Intermediate 3, was slowly added at a temperature of 0° C. Then, TLC was used to determine when the starting material had been removed. When the starting material was finally removed, the addition of bromine was stopped. The reaction mixture was then stirred for an additional 10 minutes, and the reaction was stopped.

A small amount of acetone was added to the reaction mixture to quench the bromine, and then an extraction process was performed using water and $CHCl_3$ in a volumetric ratio of 2:1. The collected organic layer was dried over $MgSO_4$ and concentrated. The concentrated product was precipitated using MeOH. As a result, 4.2 g (Yield: 73%) of Intermediate 4 was obtained.

3) Synthesis of Compound 9

3.13 g (8.54 mmol) of Intermediate 4, 1.15 g (3.4 mmol) of N,N-diphenylbenzidine, 1.0 g of sodium tert-butoxide, 0.115 g of $Pd_2(dba)_3$, and 0.034 g of tri(tert-butyl)phosphine were dissolved in 250 ml of toluene, and the mixture was reacted at 80° C. for 12 hours.

After the reaction was complete, the reaction mixture was cooled to room temperature and 200 ml of distilled water was added thereto. Then, an extracting process was performed using toluene and water in a volumetric ratio of 1:1. The collected organic layer was dried over $MgSO_4$ and concentrated. Silicagel column chromatography was performed on the concentrated product using an eluent of toluene and hexane in a volumetric ratio of 1:2. The obtained eluate was concentrated and dried to obtain 2.8 g (Yield: 93.5%) of Compound 9.

$^1$H NMR (300 MHz, $CDCl_3$, δ): 7.98 (2H, s), 7.79 (2H, s), 7.73 (2H, s), 4.28 (2H, s)

Assessment Example

Properties of the Material

Compound 4 and Compound 9 were each diluted to a concentration of 1 mM using toluene. Each solution was identified using an ultraviolet/visible light (UV/Vis) spectrum. In the UV/Vis spectrum, the largest absorption wavelengths of Compound 4 and Compound 9 were 357 nm and 356 nm, respectively. The Band gap of Compound 4 and Compound 9 were measured using UV absorption edges, and were determined to be 3.03 eV and 3.01 eV, respectively.

In addition, Compound 4 and Compound 9 were subjected to a thermal analysis using both thermo gravimetric analysis (TGA) and differential scanning calorimetry (DSC) methods. The TGA analysis was conducted using a Pt pan in a disposable Al pan in a $N_2$ atmosphere, and at a temperature range from about room temperature to about 600° C. (10° C./min). The DSC analysis was conducted in a disposable Al pan at a temperature range from about room temperature to about 400° C. The Td(° C.)/Tg(° C.) of Compound 4 and Compound 9 were 489(° C.)/149(° C.) and 490(° C.)/164(° C.), respectively.

The highest occupied molecular orbital (HOMO) energy bands of Compound 4 and Compound 9 were measured using an AC-2 photoelectron spectrometer that is an ionization potential measuring device. The resulting HOMO energy bands for Compound 4 and Compound 9 were 5.08 eV and 5.03 eV, respectively.

Example 1

[Formula 16]

[Formula 17]

An electroluminescent device was formed comprising an HIL formed using Compound 4, an HTL formed using the compound represented by Formula 16, and an EML formed using tris(8-quinolinolato)aluminum (Alq3. The resulting electroluminescent device comprised the following layers and respective thicknesses: ITO/compound 4 (350 Angstroms)/Formula 16 (300 Angstroms)/Formula 17 (400 Angstroms)/LiF (7 Angstroms)/Al (2000 Angstroms).

Figure 2:
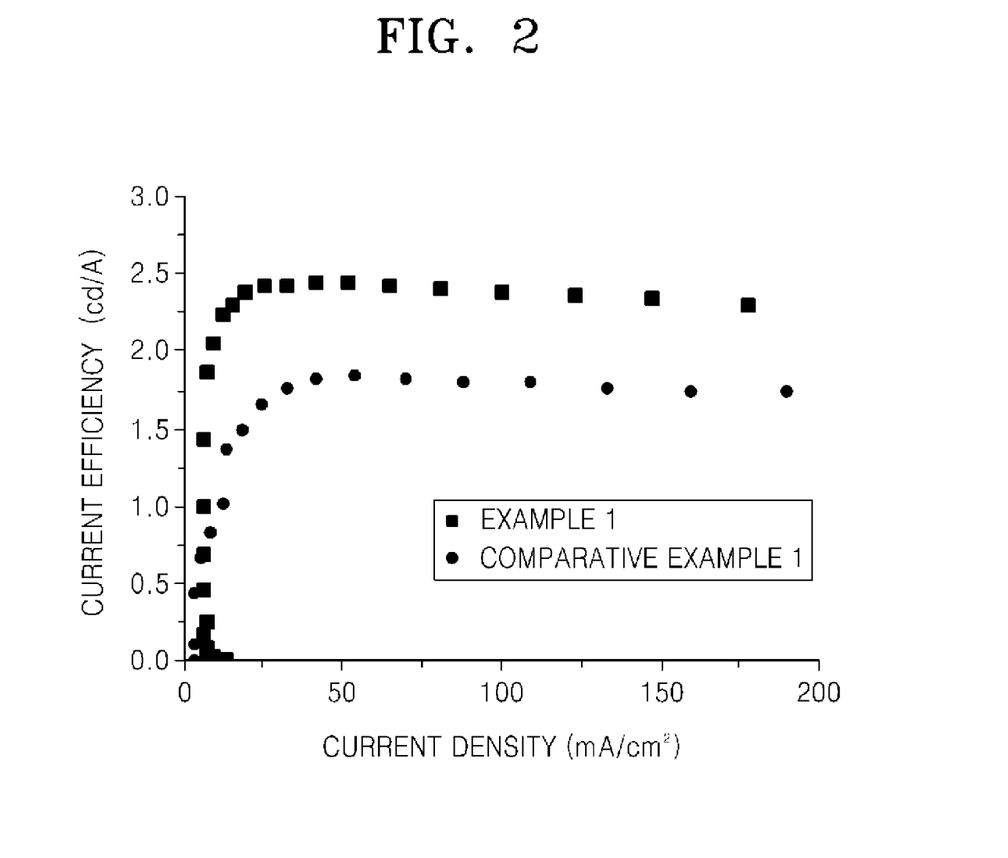
FIG. 2 is a graph of comparing the current density with the current efficiency of an exemplary organic electroluminescent device.
Figure 3:
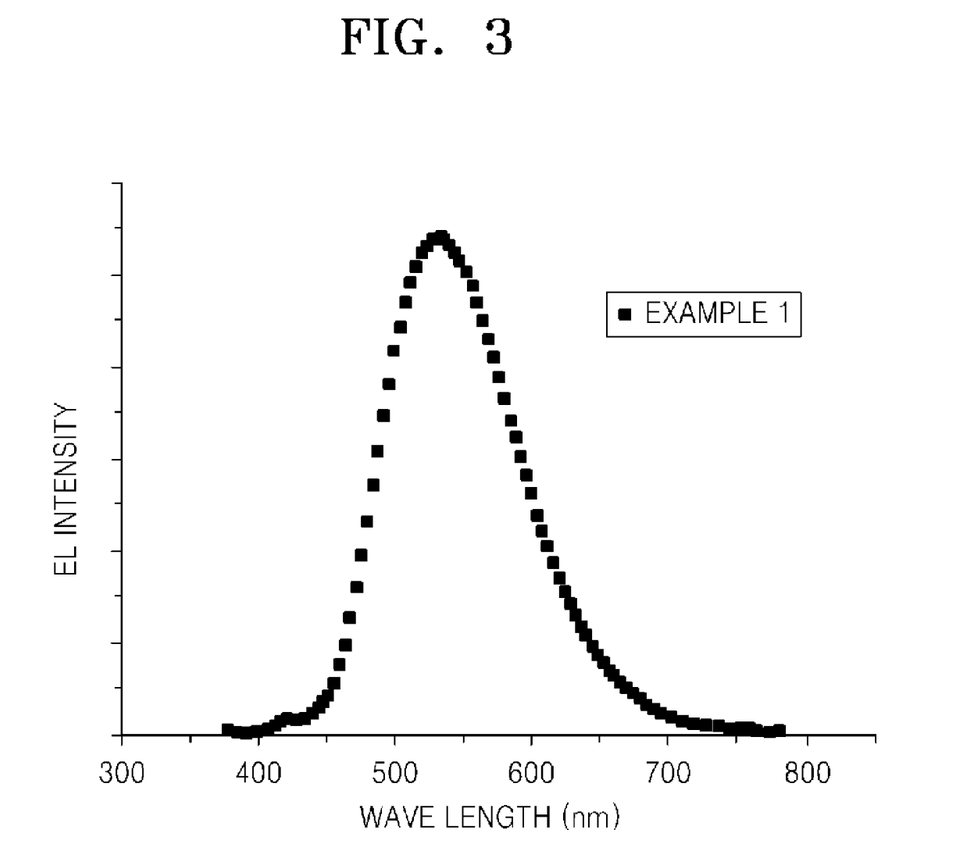
FIG. 3 is a view illustrating the emission spectrum of an exemplary organic electroluminescent device.

For the preparation of an anode, a 15 ohm per centimeter squared ($\Omega/cm^2$) (1000 Angstroms) ITO glass substrate, was first cut to a size of 50 mm×50 mm×0.7 mm, and was then sonicated in acetone isopropyl alcohol for 15 minutes, sonicated in pure water for 15 minutes, and washed using UV ozone for 30 minutes. Compound 4 (hole injection layer), and the compound represented by Formula 16 (hole transport layer), were sequentially vacuum deposited on the substrate, and the compound represented by Formula 17 was then vacuum deposited to form an EML. Then, a layer of LiF (7 Angstroms) (electron injection layer) and a layer of Al (2000 Angstroms) (cathode) were sequentially deposited on the EML to manufacture the organic electroluminescent device illustrated in FIG. 1. The organic electroluminescent device demonstrated 1300 candela per meter squared ($cd/m^2$) of green emission at a current density of 50 milliAmperes per centimeter squared ($mA/cm^2$), and with a current efficiency of 2.45 cd/A (candela per Ampere). In FIG. 2, the relationship between the current density and the current efficiency for Example 1 is compared with the results obtained for Comparative Example 1. Meanwhile the electroluminescence spectrum for Example 1 is illustrated in FIG. 3.

Example 2

An organic electroluminescent device was formed having the structure of ITO/compound 9 (350 Angstroms)/Formula 16 (300 Angstroms)/Formula 17 (400 Angstroms)/LiF (7 Angstroms)/Al (2000 Angstroms) was manufactured in the same manner as Example 1, except that the HIL was formed using Compound 9 instead of Compound 4. The organic electroluminescent device showed 1500 $cd/m^2$ of green emission at a current density of 50 $mA/cm^2$, and with a current efficiency of 2.68 cd/A.

Comparative Example 1

An organic electroluminescent device was formed having the structure of ITO/Formula 18 (350 Angstroms)/Formula 16 (300 Angstroms)/Formula 17 (400 Angstroms)/LiF (7 Angstroms)/Al (2000 Angstroms) was manufactured in the same manner as Example 1, except that the HIL was formed using Compound 18 instead of Compound 4. The organic electroluminescent device showed 1000 cd/m$^2$ of green emission at a current density of 50 mA/cm$^2$, and with a current efficiency of 1.8 cd/A.

From these results, it can be seen that an organic electroluminescent device using an HIL formed of a compound according to an exemplary embodiment demonstrated increased brightness and a higher current efficiency at the same current density, as compared to an organic electroluminescent device using an HIL formed of Compound 18 (Comparative Example 1).

A phenylphenoxazine- or phenylphenothiazine-based compound can be easily prepared, and easily dissolved. In addition, phenylphenoxazine- or phenylphenothiazine-based compounds have excellent hole injection properties and excellent thermal stability. Accordingly, an organic layer formed using the compound can provide an organic electroluminescent device having high levels of brightness and excellent current efficiency. Further, the compound is also suitable for use as an organic pigment or as an electronic material, such as a nonlinear optical material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A phenylphenoxazine- or phenylphenothiazine-based compound as represented by Formula 1:

wherein $R_1$ through $R_9$ are identical to or different from each other, and are each independently hydrogen, a halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{30}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ aralkyl group, or a substituted or unsubstituted $C_2$-$C_{30}$ heteroaryl group;

X is O or S; and

$Ar_1$ and $Ar_2$ are identical to or different from each other, and are each independently a substituted or unsubstituted $C_6$-$C_{30}$ aryl group, or a substituted or unsubstituted $C_2$-$C_{30}$ heteroaryl group.

2. The compound of claim 1, wherein the compound represented by Formula 1 is selected from compounds represented by Formula 2 through Formula 13:

[Formula 2]

[Formula 3]

[Formula 4]

[Formula 5]

[Formula 6]

[Formula 7]

[Formula 8]

[Formula 9]

-continued

3. A method of preparing a compound represented by Formula 1, the method comprising reacting a phenylphenox-azinebromide or a phenylphenothiazinebromide represented by Formula 14 with an N, N-diarylbenzidine represented by Formula 15:

wherein $R_1$ through $R_9$ are identical to or different from each other, and are each independently hydrogen, a halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{30}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ aralkyl group, or a substituted or unsubstituted $C_2$-$C_{30}$ heteroaryl group;

X is O or S; and $Ar_1$ and $Ar_2$ are identical to or different from each other, and are each independently a substituted or unsubstituted $C_6$-$C_{30}$ aryl group, or a substituted or unsubstituted $C_2$-$C_{30}$ heteroaryl group.

4. An organic electroluminescent device comprising:
a first electrode;
a second electrode; and
at least one organic layer interposed between the first electrode and the second electrode, wherein the organic layer comprises the compound of claim 1.

5. The organic electroluminescent device of claim 4, wherein the organic layer is a hole injection layer or a hole transport layer.

* * * * *